United States Patent [19]

Ascione et al.

[11] Patent Number: 5,489,431
[45] Date of Patent: Feb. 6, 1996

[54] PHOTOPROTECTIVE/COSMETIC COMPOSITIONS COMPRISING 2,4,6-TRIS[P-((2'-ETHYLHEXYL)OXY-CARBONYL)ANILINO]-1,3,5-TRIAZINE AND DIOCTYL MALATE

[75] Inventors: Jean-Marc Ascione, Paris; Delphine Allard, Colombes, both of France

[73] Assignee: L'Oreal, Paris, France

[21] Appl. No.: 463,503

[22] Filed: Jun. 5, 1995

[30] Foreign Application Priority Data

Jun. 3, 1994 [FR] France ................................. 94 06834

[51] Int. Cl.$^6$ ................................................... A61K 7/40
[52] U.S. Cl. ............................................... 424/401; 424/59
[58] Field of Search ..................... 424/401, 59; 514/938, 514/844

[56] References Cited

U.S. PATENT DOCUMENTS 5,102,660  4/1992  Forestier et al. ...................... 424/401

FOREIGN PATENT DOCUMENTS 0457687  11/1991  European Pat. Off. .

*Primary Examiner*—Thurman K. Page
*Assistant Examiner*—Sharon L. Howard
*Attorney, Agent, or Firm*—Burns, Doane, Swecker & Mathis

[57] ABSTRACT

Topically applicable sunscreen/cosmetic compositions having improved cosmetic properties and well suited for enhanced photoprotection of human skin and/or hair against the damaging effects of UV-A and UV-B irradiation, particularly solar radiation, comprise (i) a photoprotecting effective amount of 2,4,6-tris[p-((2'-ethylhexyl)oxycarbonyl)anilino]-1,3,5-triazine and (ii) the oil dioctyl malate, in an amount effective to itself substantially dissolve the total amount of triazine compound (i), in a cosmetically acceptable vehicle, diluent or carrier therefor.

21 Claims, No Drawings

PHOTOPROTECTIVE/COSMETIC COMPOSITIONS COMPRISING 2,4,6-TRIS-[P-((2'-ETHYLHEXYL)OXYCARBONYL)ANILINO]-1,3,5-TRIAZINE AND DIOCTYL MALATE

CROSS-REFERENCE TO COMPANION APPLICATIONS

Copending applications Ser. No. 08/463,221 [Attorney Docket No. 016800-028], Ser. No. 08/463,221 [Attorney Docket No. 016800-029], Ser. No. 08/463,505 [Attorney Docket No. 016800-031], Ser. No. 08/463,762 [Attorney Docket No. 016800-032], Ser. No. 08/463,304 [Attorney Docket No. 016800-033], Ser. No. 08/463,508 [Attorney Docket No. 016800-034], Ser. No. 08/461,015 [Attorney Docket No. 016800-035], Ser. No. 08/463,507 [Attorney Docket No. 016800-036], Ser. No. 08/464,940 each filed concurrently herewith and each assigned to the assignee hereof.

BACKGROUND OF THE INVENTION

1. Technical Field of the Invention

The present invention relates to novel cosmetic compositions for topical application, for the photoprotection of the skin and/or the hair against ultraviolet radiation (such compositions hereinafter simply designated "sunscreen," "sunscreen/cosmetic" or "photoprotective/sunscreen" compositions), and to the use of same for the cosmetic applications indicated above.

This invention more especially relates to the aforesaid sunscreen/cosmetic compositions imparting enhanced photoprotection and exhibiting improved cosmetic properties, comprising, in a cosmetically acceptable vehicle, carrier or diluent, typically an oil-in-water emulsion, combinatory immixture of (i) the lipophilic organic sunscreen compound 2,4,6-tris[p-((2'-ethylhexyl)oxycarbonyl)anilino]- 1,3,5-triazine and (ii) a judiciously selected specific oil, present in a predetermined amount, namely, dioctyl malate.

2. Description of the Prior Art

It is well known to this art that light radiation of wavelengths of from 280 nm to 400 nm promotes tanning of the human epidermis, and that irradiation of wavelengths of from 280 to 320 nm, i.e., UV-B irradiation, causes erythema and burning of the skin which can impair the development of a natural tan; hence, such UV-B radiation must thus be screened from the skin.

It is also known to this art that UV-A radiation, of wavelengths from 320 to 400 nm, which tans the skin, also adversely affects it, in particular in the event of sensitive skin or a skin which is continually exposed to solar radiation.

UV-A rays cause, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of cosmetic compositions intended for the photoprotection (UV-A and/or UV-B) of human skin are known to this art.

These photoprotective/sunscreen compositions are typically oil-in-water emulsions (namely, a cosmetically acceptable vehicle, carrier or diluent comprising an aqueous continuous dispersing phase and an oily discontinuous dispersed phase) which contains, in various concentrations, one or more standard lipophilic and/or hydrophilic organic sunscreen compounds capable of selectively absorbing harmful or deleterious UV radiation. These sunscreen compounds (and the amounts thereof) are selected as a function of the desired sun protection factor (the sun protection factor (SPF) being expressed mathematically by the ratio of the irradiation time required to attain the erythema-forming threshold with the UV screening agent to the time required to attain the erythema-forming threshold in the absence of UV screening agent).

One organic sunscreen compound having desirable properties and which to date has been widely used is 2,4,6-tris [p-((2'-ethylhexyl)oxycarbonyl)anilino]-1,3,5-triazine, a lipophilic sunsceen compound which is highly active in the UV-B range, photostable and water-resistant. This compound is marketed under the trademark "UVINUL T 150" by BASF. Nonetheless, in the absence of reinforcement provided by other sunscreen agents, its photoprotective power is fairly limited in the usual cosmetic vehicles containing oils, such as oxyethylenated or oxypropylenated fatty mono- or polyalcohols ("Cetiol HE" marketed by Henkel or "Witconol APM" marketed by Witco). In addition, the cosmetic properties associated therewith are generally regarded as unsatisfactory.

SUMMARY OF THE INVENTION

It has now unexpectedly and surprisingly been determined that the photoprotective power and cosmetic properties of 2,4,6-tris[p-((2'-ethylhexyl)oxycarbonyl)anilino]- 1,3,5-triazine are conspicuously improved by formulating same with a particular oil, i.e., dioctyl malate, in an amount such that said dioctyl malate is itself capable of dissolving the entirety of said lipophilic triazine sunsceen.

Briefly, the present invention features novel photoprotective/cosmetic compositions comprising, in a cosmetically acceptable vehicle, diluent or carrier, (i) an effective sunscreen amount of 2,4,6-tris[p-((2'-ethylhexyl)oxycarbonyl)anilino]- 1,3,5-triazine, and (ii) an amount of dioctyl malate effective to itself dissolve the total amount of said triazine compound (i).

The present invention also features the use of such compositions as, or for the formulation of, sunscreen/cosmetic compositions intended for the photoprotection of the skin and/or the hair against ultraviolet irradiation, in particular solar radiation.

The cosmetic treatment for the photoprotection of the skin and/or the hair against ultraviolet irradiation, in particular solar radiation, comprises topically applying thereto an effective amount of a sunscreen/cosmetic composition as described above.

This invention, thus, also features the use of dioctyl malate for improving the photoprotective capacity and/or cosmetic properties of sunscreen/cosmetic compositions comprised of 2,4,6-tris[ p-((2'-ethylhexyl)oxycarbonyl)anilino]-1,3,5triazine.

DETAILED DESCRIPTION OF BEST MODE AND PREFERRED EMBODIMENTS OF THE INVENTION

More particularly according to the present invention, 2,4,6-tris[p-((2'-ethylhexyl)oxycarbonyl)anilino]- 1,3,5-triazine (compound A) is a sunscreen compound that is per se known to this art and is active in the UV-B range, is a solid material and is marketed under the trademark "UVINUL T 150" by BASF. This compound has the following structural formula (I):

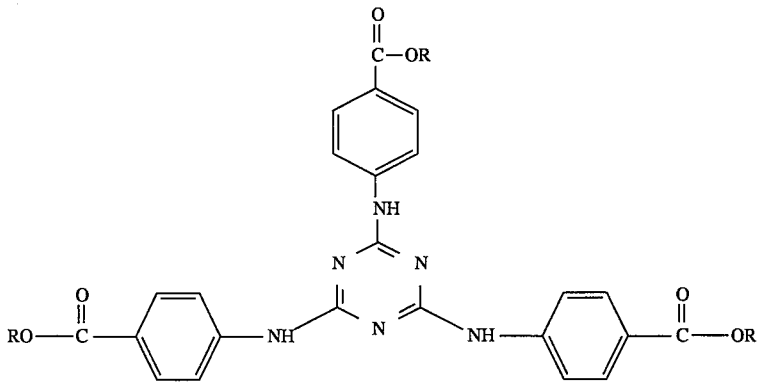

in which R is a 2-ethylhexyl radical.

The triazine sunscreen compound (i) is advantageously present in the compositions according to the invention at a concentration ranging from 0.1% to 10% by weight, and preferably from 0.5% to 5% by weight, relative to the total weight of the composition. In an important embodiment of this invention, said triazine compound (i) must exist in the final sunscreen/cosmetic compositions in an entirely, or substantially entirely, dissolved state.

The dioctyl malate according to the present invention is a known compound, designated Dioctyl Malate in the CTFA nomenclature (5th edition, 1993), and which has the following structural formula (II):

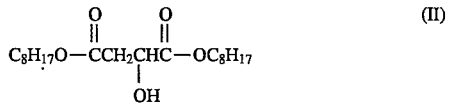

This compound is commercially available and is marketed under the trademark "Ceraphyl 45" by Mallinckrodt.

This specific oil is advantageously present in the final sunscreen/cosmetic compositions at a concentration ranging from 0.5% to 50% by weight relative to the total weight of the composition, and preferably from 2% to 30% by weight thereof. It is an essential characteristic of the compositions according to the invention that the dioctyl malate must be present in an amount such that it itself is sufficient to dissolve the total amount, or substantially total amount, of the 2,4,6-tris[p-((2'-ethylhexyl)oxycarbonyl)anilino]- 1,3,5-triazine present therein. This minimum amount of solvent oil, intended to provide for the complete and stable dissolution of the solid sunscreen compound (i), can readily be conventionally determined from the solubility parameters of said screening compound in this solvent.

Moreover, the concentrations and ratios of the sunscreen compound (i) and the oil (ii) are typically selected such that the sun protection factor of the final composition is preferably at least 2.

In a preferred embodiment of the present invention, the cosmetically acceptable vehicle, diluent, carrier or support in which the compound (i) and oil (ii) are formulated is an emulsion of oil-in-water type.

Of course, the sunscreen/cosmetic compositions according to the invention may contain one or more additional hydrophilic or lipophilic sunscreen agents active in the UV-A and/or UV-B range (absorbers), other than the two sunscreen compounds indicated above. Exemplary of such additional sunscreens are cinnamic derivatives, salicylic derivatives, camphor derivatives, triazine derivatives, benzophenone derivatives, dibenzoylmethane derivatives, β,β-diphenylacrylate derivatives, p-aminobenzoic acid derivatives, and the sunscreen polymers and sunscreen silicones described in WO-93/04,665. Other examples of organic sunscreen agents are described in EO-A-0,487,404.

The compositions according to the invention may also contain agents for the artificial tanning and/or browning of the skin (self-tanning agents) such as, for example, dihydroxyacetone (DHA).

The cosmetic compositions according to the invention may also contain pigments or, alternatively, nanopigments (average size of the primary particles: generally ranging from 5 nm to 100 nm, preferably from 10 to 50 nm) of coated or uncoated metal oxides such as, for example, nanopigments of titanium dioxide (amorphous or crystallized in rutile and/or anatase form), of iron oxide, of zinc oxide, of zirconium oxide or of cerium oxide, which are all photoprotective agents that are per se well known to this art and which are effective by physical blocking (reflection and/or diffusion) of the UV irradiation. Conventional coating agents include, moreover, alumina and/or aluminum stearate. Such coated or uncoated metal oxide nanopigments are described, in particular, in EP-A-0,518,772 and EP-A-0,518,773.

The compositions of the invention may additionally comprise conventional cosmetic additives and adjuvants selected especially from among fats, organic solvents, ionic or nonionic thickening agents, softeners, antioxidants and especially anti-free-radical antioxidants, opacifying agents, stabilizing agents, emollients, silicones, α-hydroxy acids, antifoaming agents, hydrating agents, vitamins, fragrances, preservatives, surfactants, fillers, insect repellants, sequestering agents, polymers, propellants, basifying or acidifying agents, dyes and colorants, or any other ingredient usually employed in cosmetics, in particular for the production of sunscreen/cosmetic compositions in emulsion form.

The fats may comprise an oil or a wax or mixtures thereof, and may also comprise fatty acids, fatty alcohols and fatty acid esters. The oils may be selected from among animal, plant, mineral or synthetic oils and, especially, from among liquid petrolatum, paraffin oil, volatile or non-volatile silicone oils, isoparaffins, poly-α-olefins, fluoro oils and perfluoro oils. Similarly, the waxes may be selected from among animal, fossil, plant, mineral or synthetic waxes that are per se known to this art.

Exemplary organic solvents include the lower polyols and alcohols.

The thickening agents may be selected, especially, from among crosslinked polyacrylic acids, modified or unmodified guar gums and celluloses such as hydroxypropyl guar gum, methylhydroxyethylcellulose and hydroxypropylmethylcellulose.

The compositions of the invention may be formulated according to techniques well known to this art, in particular those intended for the preparation of emulsions of oil-in-water or water-in-oil type.

The subject compositions may, in particular, be in simple or complex (O/W, W/O, O/W/O or W/O/W) emulsion form such as a cream, a milk, a gel, an ointment or a cream gel, in powder form or in solid stick form and may optionally be packaged as an aerosol and may be provided in the form of a foam or a spray.

When it is an emulsion, the aqueous phase of this emulsion may comprise a nonionic vesicle dispersion prepared according to known processes (Bangham, Standish and Watkins, J. Mol. Biol, 13, 238 (1965), FR-2,315,991 and FR-2,416,008).

The cosmetic compositions of the invention are useful for protecting the human epidermis or the hair against the damaging effects of ultraviolet rays, as sunscreen compositions or as makeup products.

When the cosmetic compositions according to the invention are used for photoprotection of the human epidermis against UV rays, or as sunscreen compositions, they may be formulated as a suspension or a dispersion in solvents or fats, in the form of a nonionic vesicle dispersion or, alternatively, in the form of an emulsion, preferably of oil-in-water type, such as a cream or a milk, or in ointment, gel, cream gel, solid stick, stick, aerosol foam or spray form.

When the cosmetic compositions according to the invention are used for the photoprotection of the hair, they may be formulated as a shampoo, a lotion, a gel, an emulsion, a nonionic vesicle dispersion or a lacquer for the hair and may constitute, for example, a composition to be rinsed, to be applied before or after shampooing, before or after dyeing or bleaching, before, during or after permanent-waving or hair-straightening, a styling or treating lotion or gel, a blow-drying or hair-setting lotion or gel, or a composition for the permanent-waving or straightening, dyeing or bleaching of the hair.

When the subject compositions are used as a makeup product for the eyelashes, the eyebrows or the skin, such as an epidermal treatment cream, a foundation, a lipstick, an eyeshadow, a blush, a mascara or "eyeliner", they may be in anhydrous or aqueous, solid or pasty form, such as oil-in-water or water-in-oil emulsions, nonionic vesicle dispersions or, alternatively, suspensions.

For example, for the photoprotective/sunscreen formulations in accordance with this invention which comprise a vehicle of oil-in-water emulsion type, the aqueous phase (comprising hydrophilic sunscreen agents in particular) generally constitutes from 50% to 95% by weight, preferably from 70% to 90% by weight, relative to the total formulation, the oily phase (comprising lipophilic sunscreen agents in particular) from 5% to 50% by weight, preferably from 10% to 30% by weight, relative to the total formulation, and the (co)emulsifying agent(s) from 0.5% to 20% by weight, preferably from 2% to 10% by weight, relative to the total formulation. If desired, the fatty phase of the emulsions according to the invention may comprise only the oil (ii), i.e., only the dioctyl malate.

The cosmetic treatment of the skin or hair to protect same against the deleterious effects of UV rays, especially those contained in solar radiation, comprises applying thereto an effective amount of a sunscreen/cosmetic composition as described above.

With respect to the compositions of the prior art containing 2,4,6-tris[p-((2'-ethylhexyl)oxycarbonyl)anilino]- 1,3,5-triazine, the compositions in accordance with the invention, which contain the same sunscreen compound, but in immixture with a sufficient amount of dioctyl malate, exhibit a better spreadability and they are less sticky, less greasy and gentler on application thereof.

In order to further illustrate the present invention and the advantages thereof, the following specific examples are given, it being understood that same are intended only as illustrative and in nowise limitative.

EXAMPLE 1

A variety of photoprotective/sunscreen formulations were prepared, in the form of emulsions of oil-in-water type and which contained (the amounts are expressed in weight % with respect to the total weight of the composition):

| | |
|---|---|
| (a) 2,4,6-Tris[p-((2'-ethylhexyl)-oxycarbonyl)anilino]-1,3,5-triazine ("UVINUL T 150") (sunscreen) | 10% |
| (b) Crosslinked terpolymer: methacrylic acid/ethyl acrylate/steareth-10 allyl ether, as a 30% aqueous emulsion ("SALCARE SC 90" marketed by Allied Colloids) (emulsifier) | 5% |
| (c) oil | 20% |
| (d) Preservatives | qs |
| (e) Water | qs 100% |
| with the nature of the oil being varied. | |

Each of these emulsions was produced by dissolving the photoprotective/sunscreen agent in the fatty phase, then adding the emulsifier to this fatty phase, heated to approximately 80° C., and, lastly, adding, with rapid stirring, the aqueous phase which had been heated beforehand to the same temperature.

For each of the formulations thus prepared, the sun protection factor (SPF) associated therewith was then determined. The SPF was determined by using the in vitro technique described by B. L. Diffey et al, in J. Soc. Cosmet. Chem., 40, 127–133 (1989); this technique entailed determining the monochromatic protection factors every 5 nm over a range of wavelengths from 290 to 400 nm, and in calculating the sun protection factor from these factors according to a given mathematical equation.

The compositions of the various formulations examined and the results obtained, as a mean protection factor, are reported in Table I below:

Also, by way of comparison, the results obtained using an oil-free composition are reported:

TABLE I

| OIL | Mean SPF (standard deviation) | |
|---|---|---|
| Without | 1.2 | |
| PEG-7 Glyceryl Cocoate ("CETIOL HE" marketed by Henkel) | 3.8 (0.5) | Comparative |
| Diisopropyl Adipate | 2.8 (0.1) | |
| Dioctyl Malate ("CERAPHYL 45" marketed by Mallinckrodt) | 6.8 (0.9) | Invention |

These results clearly demonstrate the notable beneficial effect contributed by the presence of the oil in accordance with the invention to the sun protection factors of the final compositions.

Moreover, the cosmetic properties of the above composition in accordance with the invention (UVINUL T 150+ CERAPHYL 45) were compared with those of a comparative composition UVINUL T 150+CETIOL HE, also as prepared above. These cosmetic properties were assessed by three human controls (sensory analysis test) by the application to their forearms of 0.2 g of composition. These subjects then graded the effects obtained on the skin from 0 to 5, grade 5 being the maximum grade corresponding to the desired criterion (less sticky, less greasy, more easily spread, and the like). The means of the grades obtained (with their standard deviation) are reported in Table II below:

| Cosmetic property | Composition according to the invention | Comparative composition |
|---|---|---|
| Spreading on application | 2.83 (0.76) | 1.17 (0.29) |
| Greasy on application | 2.83 (0.58) | 2.33 (0.29) |
| Sticky on application | 2.33 (0.29) | 0.83 (0.76) |
| Brake | 2.83 (0.29) | 1.67 (0.29) |
| Overall preference | 3.00 (0.5) | 1.67 (0.58) |

These results demonstrate the better cosmetic properties of the compositions according to the invention.

EXAMPLE 2

A specific example of a photoprotective/sunscreen composition in accordance with the invention, in the form of an oil-in-water emulsion, is as follows:

| | |
|---|---|
| (a) 2,4,6-Tris[p-((2'-ethylhexyl)-oxycarbonyl)anilino]-1,3,5-triazine ("UVINUL T 150") | 3.5 g |
| (b) 4-tert-Butyl-4'-dibenzoylmethane ("PARSOL 1789" marketed by Givauden) (sunscreen) | 1 g |
| (c) TiO$_2$ of nanopigment grade ("MT 100 T" marketed by Tayca) | 3 g |
| (d) Dioctyl Malate ("CERAPHYL 45" marketed by Mallinckrodt) | 10 g |
| (e) Mixture of cetylstearyl alcohol and of cetylstearyl alcohol oxyethylenated with 33 moles of EO (80%/20%) ("DEHSCO T 390" marketed by Tensia) | 7 g |
| (f) Mixture of glyceryl mono- and distearate ("GELEOL COPEAUX" marketed by Gattefosse) | 2 g |
| (g) Cetyl alcohol | 1.5 g |
| (h) Polydimethylsiloxane ("SILBIONE OIL 70 047V 300" marketed by Rhône-Poulenc) | 1.5 g |
| (i) Liquid paraffin | 10 g |
| (j) Benzoates of C$_{12}$/C$_{15}$ alcohols ("FINSOLV TN" marketed by Finetex) | 4 g |
| (k) Ethylenediaminetetraacetic acid, disodium salt-2H$_2$O ("EDETA BD" marketed by BASF) | 0.1 g |
| (l) Glycerol | 20 g |
| (m) Preservatives | qs |
| (n) Fragrance | qs |
| (o) Water | qs 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition adopted for the photoprotection of human skin and/or hair, comprising (i) a photoprotecting effective amount of 2,4,6-tris[p-((2'-ethylhexyl)oxycarbonyl)anilino]-1,3,5-triazine and (ii) the oil dioctyl malate, in an amount effective to itself substantially dissolve the total amount of said triazine compound (i), in a cosmetically acceptable vehicle, diluent or carrier therefor.

2. The sunscreen/cosmetic composition as defined by claim 1, comprising from 0.1% to 10% by weight of said triazine compound (i).

3. The sunscreen/cosmetic composition as defined by claim 2, comprising from 0.5% to 5% by weight of said triazine compound (i).

4. The sunscreen/cosmetic composition as defined by claim 2, comprising from 0.5% to 50% by weight of said dioctyl malate (ii).

5. The sunscreen/cosmetic composition as defined by claim 3, comprising from 2% to 30% by weight of said dioctyl malate (ii).

6. The sunscreen/cosmetic composition as defined by claim 1, comprising an oil-in-water emulsion.

7. The sunscreen/cosmetic composition as defined by claim 1, comprising a water-in-oil emulsion.

8. The sunscreen/cosmetic composition as defined by claim 1, further comprising at least one additional hydrophilic or lipophilic organic UV-A and/or UV-B sunscreen.

9. The sunscreen/cosmetic composition as defined by claim 8, further comprising at least one cinnamic derivative, salicylic derivative, camphor derivative, triazine derivative, benzophenone derivative, dibenzoylmethane derivative, β,β-diphenylacrylate derivative, p-aminobenzoic acid derivative, sunscreen polymer, or sunscreen silicone.

10. The sunscreen/cosmetic composition as defined by claim 1, further comprising a photoprotecting effective amount of particulates of at least one inorganic pigment or nanopigment.

11. The sunscreen/cosmetic composition as defined by claim 10, said at least one pigment or nanopigment comprising titanium dioxide, zinc oxide, iron oxide, zirconium oxide, cerium oxide, or mixture thereof.

12. The sunscreen/cosmetic composition as defined by claim 1, further comprising at least one active agent for the artificial tanning and/or browning of human skin.

13. The sunscreen/cosmetic composition as defined by claim 1, further comprising at least one cosmetically acceptable adjuvant or additive.

14. The sunscreen/cosmetic composition as defined by claim 13, said at least one adjuvant or additive comprising a fat, organic solvent, ionic or nonionic thickening agent, softener, antioxidant, anti-free-radical antioxidant, opacifying agent, stabilizing agent, emollient, silicone, α-hydroxy acid, anti-foaming agent, hydrating agent, vitamin, fragrance, preservative, surfactant, filler, sequestering agent, polymer, propellant, insect repellent, basifying or acidifying agent, dye, colorant, or mixture thereof.

15. The sunscreen/cosmetic composition as defined by claim 1, comprising a nonionic vesicle dispersion, emulsion, cream, milk, gel, cream gel, ointment, suspension, dispersion, powder, solid stick, foam or spray.

16. The sunscreen/cosmetic composition as defined by claim 1, comprising a makeup.

17. The sunscreen/cosmetic composition as defined by claim 16, comprising an anhydrous or aqueous solid or paste, emulsion, suspension, or dispersion.

18. The sunscreen/cosmetic composition as defined by claim 1, comprising a shampoo, lotion, gel, emulsion, nonionic vesicle dispersion, hair lacquer, or rinse.

19. The sunscreen/cosmetic composition as defined by claim 1, having a sun protection factor of at least 2.

20. A method for protecting human skin and/or hair against the deleterious effects of ultraviolet irradiation, comprising topically applying thereto an effective amount of the sunscreen/cosmetic composition as defined by claim 1.

21. A method for protecting human skin and/or hair against the deleterious effects of solar radiation, comprising topically applying thereto an effective amount of the sunscreen/cosmetic composition as defined by claim 1.

* * * * *